(12) United States Patent
Jansen et al.

(10) Patent No.: US 8,466,111 B2
(45) Date of Patent: Jun. 18, 2013

(54) CYCLOPENTA{G}QUINAZOLINE DERIVATIVES FOR THE TREATMENT OF RHEUMATOID ARTHRITIS OR ACUTE MYELOID LEUKAEMIA

(75) Inventors: Gerrit Jansen, Amsterdam (NL); Ann Jackman, Sutton (GB)

(73) Assignee: BTG International Limited, London (GB)

( * ) Notice: Subject to any disclaimer, the term of this patent is extended or adjusted under 35 U.S.C. 154(b) by 247 days.

(21) Appl. No.: 12/735,743

(22) PCT Filed: Mar. 13, 2009

(86) PCT No.: PCT/GB2009/000687
§ 371 (c)(1),
(2), (4) Date: Dec. 7, 2010

(87) PCT Pub. No.: WO2009/115776
PCT Pub. Date: Sep. 24, 2009

(65) Prior Publication Data
US 2011/0190211 A1   Aug. 4, 2011

(30) Foreign Application Priority Data

Mar. 18, 2008  (GB) .................................. 0805035.3
Mar. 18, 2008  (GB) .................................. 0805036.1

(51) Int. Cl.
*A61K 38/00*   (2006.01)
*A61K 38/05*   (2006.01)
*A61P 35/02*   (2006.01)

(52) U.S. Cl.
USPC ...................................... 514/19.6; 514/21.91

(58) Field of Classification Search
None
See application file for complete search history.

(56) References Cited

U.S. PATENT DOCUMENTS 5,747,499 A * 5/1998 Bavetsias et al. ............. 514/267

FOREIGN PATENT DOCUMENTS

| WO | WO 03/020300 A | 3/2003 |
| WO | WO 03/020748 A | 3/2003 |
| WO | WO 03/072091 A | 9/2003 |

OTHER PUBLICATIONS

Form PCT/IB/326, Notification Concerning Transmittal of International Preliminary Report on Patentability; PCT International Preliminary Report on Patentability, International Application No. PCT/GB2009/000687, mailed Sep. 30, 2010 (9 pgs).
Henderson, E.A., et al; "Targeting the alpha-folate receptor with cyclopenta[g]quinazoline-ba sed inhibitors of thymidylate synthase"; *Bioorganic & Medicinal Chemistry*, Elsevier Science Ltd., GB, vol. 14, No. 14, pp. 5020-5042 (2006) XP025133399.
Jackman, A.L., et al; "Antifolates targeted specifically to the folate receptor"; *Advanced Drug Delivery Reviews*; vol. 56, No. 8, pp. 1111-1125 (2004) XP002527440.
Gibbs, D.D., et al; "BGC 945, a novel tumor-selective thymidylate synthase inhibitor targeted to alpha-folate receptor-overexpressing tumors"; *Cancer Research*, vol. 65, No. 24, pp. 11721-11728 (2005) XP002527441.
Theti, D.S., et al; "Selective delivery of CB300638, a cyclopenta[g]quinazoline-based thymidylate synthase inhibitor into human tumor cell lines overexpressing the alpha-isoform of the folate receptor"; *Cancer Research*, vol. 63, No. 13, pp. 3612-3618 (2003) XP002527442.
Nakashima-Matsushita, N., et al; "Selective expression of folate receptor beta and its possible role in methotrexate transport in synovial macrophages from patients with rheumatoid arthritis"; *Arthritis and Rheumatism*, Lippincott, PA, US, vol. 42, No. 8, pp. 1609-1616 (1999) XP002284073.
Xin, W., et al; Differential stereospecificities and affinities of folate receptor isoforms for folate compounds and antifolates; *Biochemical Pharmacology*, Pergamon, Oxford, GB, vol. 44, No. 9, pp. 1898-1901 (1992) XP025567617.
Brigle, K.E., et al; "Increased expression and characterization of two distinct folate binding proteins in murine folate binding proteins in murine erythroleukemia cells", *Biochemical Pharmacology*, Pergamon, Oxford, GB, vol. 47, No. 2, pp. 337-345 (1994) XP023764830.

* cited by examiner

*Primary Examiner* — Marcela M Cordero Garcia
(74) *Attorney, Agent, or Firm* — Nixon & Vanderhye

(57) ABSTRACT

A cyclopenta[g]quinazoline derivative, containing an L-Glu-γ-D-Glu dipeptide group, of formula (I): wherein $R^1$ is amino, $C_{1-4}$ hydroxyalkyl, $C_{1-4}$ fluoroalkyl or methoxy-$C_{1-4}$-alkyl; $R^2$ is hydrogen, $C_{1-4}$ alkyl, $C_{3-4}$ alkenyl, $C_{3-4}$ alkynyl, $C_{2-4}$ hydroxyalkyl $C_{2-4}$ halogenoalkyl or $C_{1-4}$ cyanoalkyl; and Ar is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy, the compound (I) optionally being in the form of a pharmaceutically acceptable salt or ester; may be used for the treatment of rheumatoid arthritis or acute myeloid leukaemia.

13 Claims, 5 Drawing Sheets

CYCLOPENTA{G}QUINAZOLINE DERIVATIVES FOR THE TREATMENT OF RHEUMATOID ARTHRITIS OR ACUTE MYELOID LEUKAEMIA

This application is the U.S. national phase of International Application No. PCT/GB2009/000687 filed 13 Mar. 2009 which designated the U.S. and claims priority to British Application Nos. 0805035.3 filed 18 Mar. 2008, and 0805036.1 filed 18 Mar. 2008, the entire contents of each of which are hereby incorporated by reference.

BACKGROUND OF THE INVENTION

This invention relates to the use of cyclopenta[g]quinazoline derivatives. More particularly it relates to cyclopenta[g] quinazoline derivatives for the treatment of rheumatoid arthritis (RA) and acute myeloid leukaemia (AML).

Cyclopenta[g]quinazoline derivatives showing a good level of activity both as regards their ability to inhibit thymidylate synthase (TS) and also as regards their anticancer activity against various cell lines have been developed.

WO 94/11354 A1 (British Technology Group Limited) discloses tricyclic compounds of formula:

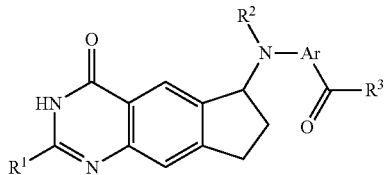

wherein $R^1$ is hydrogen, amino, $C_{1-4}$ alkyl, $C_{1-4}$ alkoxy, $C_{1-4}$ hydroxyalkyl or $C_1$—$_4$ fluoroalkyl;

$R^2$ is hydrogen, $C_{1-4}$ alkyl, $C_{3-4}$ alkenyl, $C_{3-4}$ alkynyl, $C_{2-4}$ hydroxyalkyl $C_{2-4}$ halogenoalkyl or $C_{1-4}$ cyanoalkyl;

Ar is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of one of the following formulae:

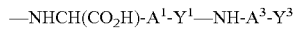
—NHCH(CO$_2$H)-A$^1$-Y$^1$—NH-A$^3$-Y$^3$ or $R^3$ is a N-linked naturally-occurring amino acid selected from the group consisting of L-alanine, L-leucine, L-isoleucine, L-valine and L-phenylalanine. Among the compounds disclosed is the L-Glu-γ-D-Glu compound CB300638, also mentioned in *Clinical Cancer Research*, 5, November 1999 (Supplement) at #566 (Theti et al.) and *Proceedings of the American Association for Cancer Research*, 41, March 2000 at #33 (Jackman et al.), as well as in *J. Med. Chem.*, 2000, 43, 1910-1926, where it is disclosed on page 1923 as compound 7b.

WO 95/30673 A1 (British Technology Group Limited) discloses cyclopenta[g]quinazolines of formula:

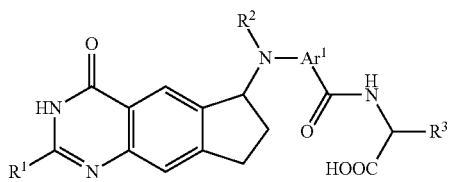

wherein $R^1$ is hydrogen, amino, $C_{1-4}$ alkyl, $C_{1-4}$ alkoxy, $C_{1-4}$ hydroxyalkyl or $C_1$—$_4$ fluoroalkyl;

$R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of one of the following formulae:

-A$^1$-Ar$^2$-A$^2$-Y$^1$-A$^5$-CON(R)CH(Y$^4$)Y$^5$-A$^8$-X—Ar$^4$

The α-isoform of the folate receptor (α-FR; membrane-associated folate-binding protein) is a glycosylphosphatidylinositol anchored cell membrane protein that has very high affinity for folic acid and the more biologically relevant reduced—folates (Kd~0.1 nM). The mechanism of folate internalization is receptor-mediated endocytosis. The α-FR is overexpressed in many carcinomas, particularly those of ovarian origin where it is overexpressed highly and homogeneously in 90% of cases; see *Cancer Res.* 51, 5329-5338, 1991 (Campbell et al., 1991). Furthermore, high α-FR expression has been linked to aggressive, platinum resistant disease and poor prognosis—see *Int. J. Cancer* 74, 193-198, 1997 and *Int. J. Cancer* 79, 121-126, 1998 (both Toffoli et al.). The β-isoform is widely expressed in tumours of epithelial and non-epithelial origin with expression levels being generally low/moderate and high, respectively, reviewed in *Critical Rev. Therap. in Drug Carrier Systems* 15, 587-627, 1998 (Reddy and Low).

Folate receptors (α and β) are expressed in some adult normal tissues (low to moderate expression). Certain compounds within the general class of cyclopenta[g]quinazolines have been reported to have a high level of selectivity for α-folate receptor expressing human tumour cell lines versus the affinity for the RFC (reduced-folate carrier). Such compounds are disclosed in WO 03/020300 A1, WO 03/020706 A1 and WO 03/020748 A1 (BTG International Limited). Among the compounds disclosed is the L-Glu-γ-D-Glu compound CB300945, also mentioned in *Tetrahedron*, 63 (7), 12 Feb. 2007, 1537-1543 (Bavetsias et al.) and *Cancer Research* 65, 15 Dec. 2005, 11721-11728 (Gibbs et al.).

FR-β is normally found in placenta tissues and in hematopoietic cells, where it is expressed in the myelomonocytic lineage and is particularly elevated during neutrophil maturation or during monocyte or macrophage activation. However, the FR-β expressed on normal hematopoietic cells, unlike that on activated macrophages for example, is non-functional in that it cannot bind and internalize folate. FR-β is expressed on malignant cells from patients with chronic myelogenous leukaemia (CML), and on malignant cells from approximately 70% of patients with AML.

WO 03/072091-A1 (The Ohio State University Research Foundation) uses the discovery that expression of FR-β is increased in malignant cells from myeloid leukaemia patients by FR-β inducers. The FR-β expressed in myeloid leukaemia cells, preferably AML cells, is functional in that it binds and internalizes folate, unlike the FR-β expressed in the majority of normal hematopoietic cells which is non-functional. Such functional FR-β is a target for folate-conjugated therapeutics.

Jansen, in an abstract from the 13th International Symposium on Chemistry & Biology of Pteridines & Folates entitled "Antifolates in chronic inflammatory diseases/rheumatoid arthritis: what can we learn from cancer and vice versa," *Pteridines*, 16: 46, 2005, indicates that methotrexate (MTX) is the anchor drug in treatment regimens for patients with rheumatoid arthritis. He furthermore speculates that cyclopenta[g]quinazoline-based TS inhibitors exhibited binding affinities close to folic acid and could thus be interesting FR-targeted drugs in the treatment of cancer as well as inflammatory diseases.

SUMMARY OF THE INVENTION

We have now discovered that certain compounds within the general class of cyclopenta[g]quinazolines have an unexpectedly high level of selectivity for β-folate receptor expressing cell lines. Such a compound has two structural features, that is to say a three-ring structure and modification to the glutamate side chain when compared with folic acid. Accordingly the present invention comprises a cyclopenta[g]quinazoline derivative, containing an L-Glu-γ-D-Glu dipeptide group, of formula (I):

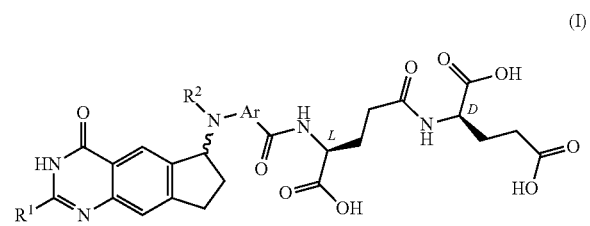

wherein:

$R^1$ is amino, $C_{1-4}$ alkyl, $C_{1-4}$ hydroxyalkyl, $C_{1-4}$ fluoroalkyl or methoxy-$C_{1-4}$-alkyl;

$R^2$ is $C_{1-4}$ alkyl, $C_{3-4}$ alkenyl, $C_{3-4}$ alkynyl, $C_{2-4}$ hydroxyalkyl $C_{2-4}$ halogeno-alkyl or $C_{1-4}$ cyanoalkyl; and Ar is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy.

the compound (I) optionally being in the form of a pharmaceutically acceptable salt or ester;

for the treatment of rheumatoid arthritis or acute myeloid leukaemia.

The compounds of the invention display one or more of the following advantages:

1. high selectivity for cells over-expressing the β-FR, when grown in physiological concentrations of folate and possessing normal expression of the RFC;
2. a potent TS inhibition, a low affinity for the RFC and a moderate to high affinity for the β-FR;
3. TS-specific activity and are resistant to in vivo hydrolases; and
4. selective activity in primary Chinese Hamster Ovarian cell line screen with moderate β-FR expression.

In this specification the terms alkyl, alkenyl and alkynyl include both straight and branched chain groups but references to individual alkyl groups, such as propyl, are specific for the straight chain group only. An analogous convention applies to other generic terms. Moreover, the numbering system used for the cyclopenta[g]quinazoline nucleus is the conventional one as shown below:

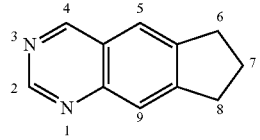

Amino-acid residues are designated herein in the standard manner (*Pure and Applied Chemistry*, 1974, 40, 317 and *European Journal of Biochemistry*, 1984, 138, 9). Thus, for example, γ-glutamyl denotes the radical $H_2NCH(CO_2H)CH_2CH_2CO-$ or $-NHCH(CO_2H)CH_2CH_2CO-$ according to the context, the carbon atoms in these radicals being numbered from the carbon atom of the α-carboxyl group as position 1.

It will be observed that a cyclopenta[g]quinazoline of the invention contains at least three asymmetric carbon atoms [present at the point of attachment of the group $-N(R^2)-$ to the tricyclic ring system and at the α-carbon atoms of the group L-Glu-γ-D-Glu] and can therefore exist in racemic and optically active forms. It is to be understood that this invention encompasses both racemic and optically active forms, it being a matter of common general knowledge how such optically active forms may be obtained by stereospecific synthesis or by separation of a mixture of isomeric compounds. It will be appreciated that one isomer may be of more interest than another owing to the nature of the activity which it exhibits or owing to superior physical properties, for example aqueous solubility.

It is also to be understood that a cyclopenta[g]quinazoline of the formula (I) may exhibit the phenomenon of tautomerism and that the formulae shown in this specification represent only one of the possible tautomeric forms.

It is also to be understood that certain cyclopenta[g]quinazolines of the formula (I) can exist in solvated as well as unsolvated forms such as, for example, hydrated forms.

A suitable value for $R^1$ or $R^2$ when it is $C_{1-4}$ alkyl, or for a $C_{1-4}$ alkyl substituent which may be present on Ar, is, for example, methyl, ethyl, propyl or isopropyl.

A suitable value for a $C_{1-4}$ alkoxy substituent which may be present on Ar is, for example, methoxy, ethoxy, propoxy, isopropoxy or butoxy.

A suitable value for a halogeno substituent which may be present on Ar is, for example, fluoro, chloro or bromo.

A suitable value for $R^2$ when it is $C_{3-4}$ alkenyl is, for example, prop-2-enyl, but-2-enyl, but-3-enyl or 2-methylprop-2-enyl; and when it is $C_{3-4}$ alkynyl is, for example, prop-2-ynyl or but-3-ynyl.

A suitable value for $R^2$ when it is $C_{2-4}$ hydroxyalkyl is, for example, 2-hydroxyethyl or 3-hydroxypropyl; when it is $C_{2-4}$ halogenoalkyl is, for example, 2-fluoroethyl, 2-chloroethyl, 2-bromoethyl, 3-fluoropropyl, 3-chloropropyl or 3-bromopropyl; and when it is $C_{1-4}$ cyanoalkyl is, for example, cyanomethyl, 2-cyanoethyl or 3-cyanopropyl.

A suitable value for Ar when it is phenylene is, for example, 1,3- or 1,4-phenylene, especially 1,4-phenylene.

A suitable value for Ar when it is thiophenediyl is, for example, thiophene-2,4-diyl or thiophene-2,5-diyl; when it is thiazolediyl is, for example thiazole-2,4-diyl or thiazole-2,5-diyl; when it is pyridinediyl is, for example, pyridine-2,4-diyl, pyridine-2,5-diyl, pyridine-2,6-diyl or pyridine-3,5-diyl; and when it is pyrimidinediyl is, for example, pyrimidine-2,4-diyl, pyrimidine-2,5-diyl or pyrimidine-4,6-diyl.

As indicated, Ar may carry one or two substituents. A preferred level of substitution in Ar, where substitution is present, is either two substituents or especially one substituent; and the one or two substituents may conveniently be at positions adjacent to the atom bonded to the group —CO-L-Glu-γ-D-Glu, halogeno substituents such as fluoro being preferred.

A suitable pharmaceutically acceptable salt form of a cyclopenta[g]-quinazoline of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra (2-hydroxyethyl)ammonium, salt.

A suitable pharmaceutically acceptable ester form of a cyclopenta[g]quinazoline of the invention is, for example, an ester with an aliphatic alcohol of up to 6 carbon atoms, for example a methyl, ethyl or tert-butyl ester.

The compound contains three carboxyl groups. A salt or ester may be mono-acid-di-salt or -ester, di-acid-mono-salt or -ester or even tri-salt or -ester.

Preferably $R^1$ is $C_{1-4}$ alkyl or $C_{1-4}$ hydroxyalkyl. More preferably $R^1$ is methyl or, especially, hydroxymethyl.

Preferably $R^2$ is methyl, ethyl, propyl, prop-2-enyl, prop-2-ynyl, 2-hydroxy-ethyl, 2-fluoroethyl, 2-bromoethyl or 2-cyanoethyl. More preferably $R^2$ is methyl or, especially, prop-2-ynyl.

Preferably Ar is 1,4-phenylene which may optionally bear one or two substituents selected from the group consisting of chloro and especially fluoro, thiophene-2,5-diyl, thiazole-2, 5-diyl or pyridine-2,5-diyl. More preferably Ar is 1,4-phenylene or 1,4-phenylene having a 2-fluoro substituent as in 2,6-difluoro-1,4-phenylene or especially 2-fluoro-1,4-phenylene or is pyridine 2,5-diyl. Most preferably Ar is 1,4-phenylene or 2-fluoro-1,4-phenylene.

A preferred cyclopenta[g]quinazoline of the invention has the formula (I) wherein $R^1$ is $C_{1-4}$ alkyl or $C_{1-4}$ hydroxyalkyl, especially hydroxymethyl;

$R^2$ is methyl, ethyl, propyl, prop-2-enyl, prop-2-ynyl, 2-hydroxyethyl, 2-fluoroethyl, 2-bromoethyl or 2-cyanoethyl; and Ar is 1,4-phenylene which may optionally bear one or two substituents selected from the group consisting of chloro and especially fluoro, thiophene-2,5-diyl, thiazole-2,5-diyl or pyridine-2,5-diyl.

A further preferred cyclopenta[g]quinazoline of the invention has the formula (I) wherein $R^1$ is methyl or hydroxymethyl;

$R^2$ is methyl or prop-2-ynyl; and

Ar is 1,4-phenylene or 1,4-phenylene having a 2-fluoro substituent as in 2,6-difluoro-1,4-phenylene or especially 2-fluoro-1,4-phenylene or is pyridine 2,5-diyl.

An especially preferred cyclopenta[g]quinazoline of the invention has the formula (I) wherein $R^1$ is methyl or hydroxymethyl;

$R^2$ is methyl or preferably prop-2-ynyl; and

Ar is 1,4-phenylene or 2-fluoro-1,4-phenylene.

Specific particularly preferred cyclopenta[g]quinazolines of the invention are:

N-{N-{4-[N-(2-methyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid; or N-{N-{4-[N-(2-hydroxymethyl-4-oxo-3,4,7,8-tetrahydro-6H-cyclopenta[g]-quinazolin-6-yl)-N-(prop-2-ynyl) amino]benzoyl}-L-γ-glutamyl}-D-glutamic acid; or a pharmaceutically acceptable salt or ester thereof;

as well as the 6S isomers of these two compounds.

Although the compounds of the present invention can exist as a mixture of stereoisomers it is preferred that they are resolved into one optically active isomeric form. Such a requirement complicates the synthesis of the compounds and it is preferred therefore that they contain as few asymmetric carbon atoms as possible consistent with achieving the desired activity.

As indicated previously, however, the cyclopenta[g] quinazolines of the present invention contain at least three asymmetric carbon atoms. Of these, that at the 6 position of the ring system preferably has the 6S orientation rather than the 6R orientation. The preferred compounds (I) described hereinbefore thus preferably have such a configuration at this asymmetric carbon atoms or less preferably are a mixture in which one or both of these asymmetric carbon atoms is unresolved.

A cyclopenta[g]quinazoline of the invention may be prepared by any process known to be applicable to the preparation of chemically-related compounds.

A cyclopenta[g]quinazoline of the present invention may itself be active or may be a prodrug converted in vivo to an active compound. A cyclopenta[g]quinazoline of the invention may be administered to a warm-blooded animal, including a human, in the form of a pharmaceutical composition which comprises the cyclopenta[g]quinazoline in association with a pharmaceutically acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion use), for example a sterile aqueous or oily solution, emulsion or suspension. In general the above compositions may be prepared in a conventional manner using conventional excipients.

The cyclopenta[g]quinazoline will normally be administered to a warm-blooded animal at a dose within a range of 50-25000, particularly 50-5000, mg per square meter body area of the animal, i.e. approximately 1500, particularly 1-100, mg/kg. Where desired, however, dosages outside this range may be employed and, in particular, where the preferred mode of administration involving subcutaneous infusion is used then the dose range may be increased to 1-1000 mg/kg. Preferably a daily dose in the range 10-250 mg/kg is employed, particularly 30-150 mg/kg. However, the daily dose will necessarily be varied depending upon the host treated, the particular route of administration and the severity of the illness being treated. Accordingly, the optimum dosage may be determined by the practitioner who is treating any particular patient.

Accordingly the present invention also includes a method for treating rheumatoid arthritis or acute myeloid leukaemia in a patient in need of such treatment which comprises administering to said patient an effective amount of a cyclopenta[g] quinazoline derivative as defined hereinbefore.

The compound will normally be administered at a dose within the range 5-25000, particularly 5-500, mg per square meter body area of the animal, i.e. approximately 0.1-500, particularly 0.1-10, mg/kg. Where desired, however, dosages outside this range may be employed. Topical administration of a cyclopenta[g]quinazoline of the invention may be used.

Thus, for example, for topical administration a daily dose in the range, for example, of 0.1 to 10 mg/kg may be used.

Compositions containing the quinazolines may be formulated in unit dosage form, i.e. in the form of discrete portions each comprising a unit dose, or a multiple or sub-multiple of a unit dose, for example as a tablet or capsule. Such a unit dosage form may, for example, contain an amount of the cyclopenta[g]quinazoline in the range of 1-250 or 1-500 mg.

The invention is illustrated by the following Examples.

DETAILED DESCRIPTION

Example 1

Figure 1:
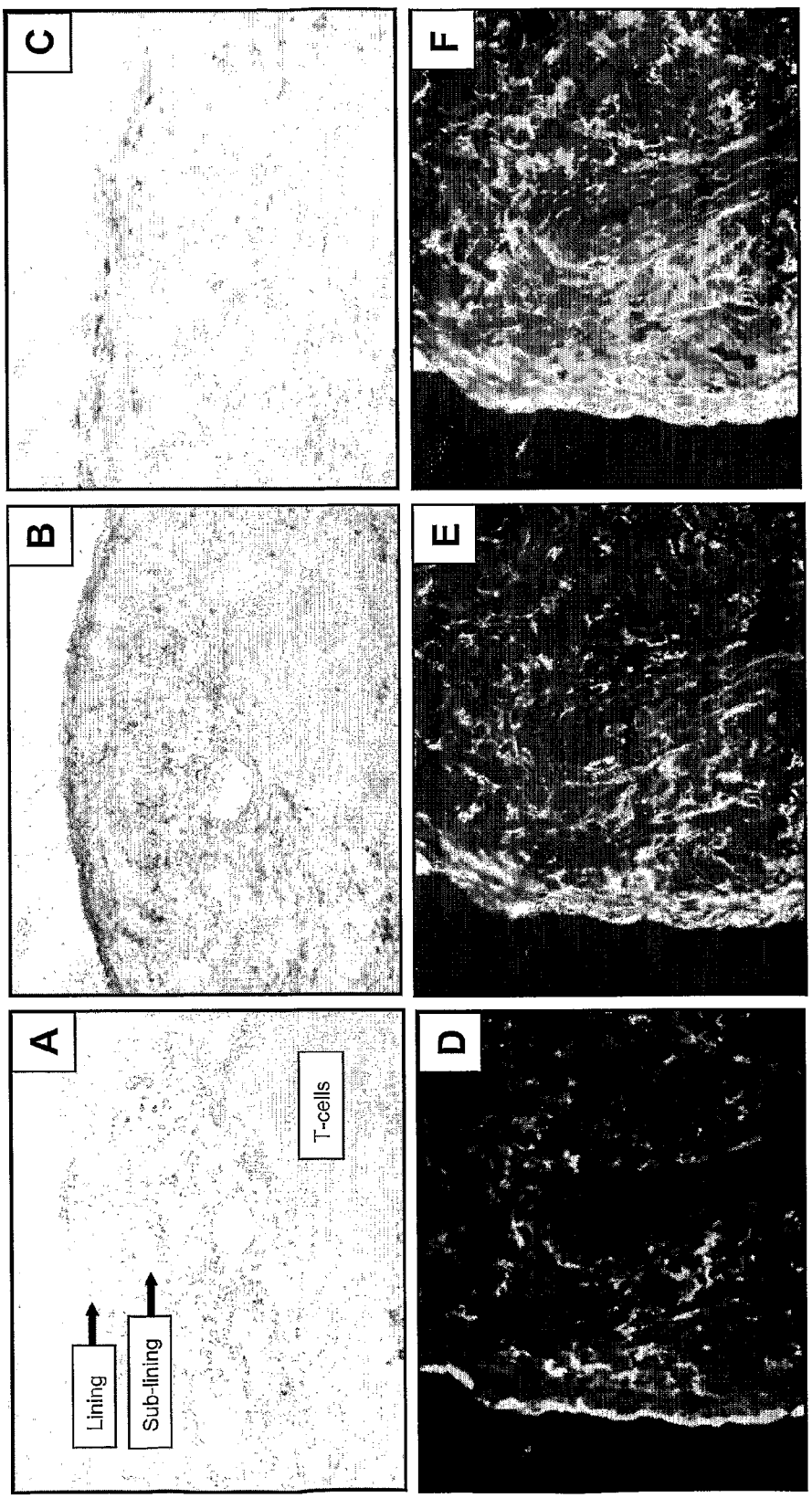
FIG. 1: Immunohistochemistry of RA-synovial tissue: Light microscopy of (A) rabbit isotype staining, (B) FR-β staining and (C) macrophage staining (3A5). Immunofluorescence (double) staining of (D) FR-β, (E) CD-68 (macrophages) and (F) merge of D and E. Of note: nuclei are stained blue (Dapi-staining).

Exploitation of Folate Receptor-β as a Potential Delivery Route for Novel Generation Folate Antagonists to Activated Macrophages in Synovial Tissue of Rheumatoid Arthritis Patients Introduction The folate antagonist methotrexate (MTX) is the anchor-drug most widely applied disease modifying antirheumatic drug (DMARD) in the treatment of patients with rheumatoid arthritis (RA). It is used either as single agent or in combination with other DMARDs (e.g. sulfasalazine and hydroxychloroquine) and MTX use is obligate in most treatment strategies involving biological agents (anti-TNFα or —CD20 monoclonal antibodies.

The first pivotal step in the cellular pharmacology of MTX is its cell entry which can be mediated by at least 3 different routes; the reduced folate carrier (RFC), membrane-associated folate receptors (MFR) or a proton-coupled (low pH) folate transporter (PCFT). The latter transporter is mainly involved in intestinal folate uptake. The other transport routes harbour physiological and pharmacological relevance for immune-competent cells by facilitating the uptake of natural reduced folate cofactors and folate antagonists like MTX. The RFC and MFR differ considerably in mechanism of (anti)folate uptake (transmembrane carrier vs. endocytosis/potocytosis), substrate specificity (low affinity folic, acid/high affinity MTX vs. high affinity folic acid/low affinity MTX) and tissue specificity (constitutive vs. restricted expression).

For MFR, three isoforms (α, β and γ) have been identified. The α-isoform of MFR is overexpressed in specific types of cancer (ovarian cancer) while the γ-isoform is a secreted protein from haematopoietic cells. Selective expression of FR-β isoform has been described on activated macrophages in inflamed synovial fluid of RA patients and animal models of arthritis. Subsequently, FR-β was recognized as an attractive target for imaging of arthritis and therapeutically for selective antibody-guided or folate-conjugate guided delivery of toxins and other small/macro-molecules. Thus far, targeting of FR with folate antagonists has only been explored on cancer cells/tissues overexpressing FRα.

Over the past decades, a second generation of folate antagonists has been designed and clinically evaluated from a perspective to circumvent common mechanisms of resistance to MTX, including impaired transport via the RFC, defective polyglutamylation, increased activity of the target enzyme DHFR and/or enhanced drug efflux. Based on this background, second generation antifolates included compounds that were more efficiently transported via RFC, were more efficiently poly-glutamylated or independent of poly-glutamylation, or target other key enzymes in folate metabolism other than DHFR, e.g. thymidylate synthase (TS) or glycinamide ribonucleotide transformylase. In the present study we set out to investigate whether distinct second generation antifolates may serve as selective targeting drugs for FR-β expressing cells in synovial tissue and/or immune-competent cells of RA patients. We identified the TS inhibitor BGC 945 as a prototypical antifolate drug that fulfilled the criteria of a high FR-β binding affinity and a low RFC affinity, thereby enabling selective drug uptake in FR-β expressing cells.

Materials and Methods

Drugs

Folic acid was obtained from Sigma Chem. Co, St. Louis, Mo., L-leucovorin from Merck Eprova, Schaffhausen, Switzerland, methotrexate from Pharmachemie, Haarlem, Netherlands and Pemetrexed/ALIMTA® (Eli Lilly) via the VUmc pharmacy department. The following folate antagonist drugs were obtained from the indicated companies/institutions; Raltitrexed/Tomudex®/ZD1694 (AstraZeneca, UK), PT523 and PT644 (Dr. A. Rosowsky, Harvard Medical School, Boston, Mass.), GW1843 (Glaxo Welcome, USA), CB300635 (Institute of Cancer Research, Sutton, UK), BGC 9331 and BGC 945 (6RS and 6S) (BTG International Limited, London, UK), 5,10-dideazatetrahydrofolate (DDATHF) (Eli Lilly, Indianapolis, Ind.), and AG2034 (Agouron/Pfizer Pharmaceuticals, San Diego, Calif.). The chemical structure of these folate antagonists are depicted in Tables 2 and 3. [3',5',7,9-$^3$H]Folic acid (20-40 Ci/mmol, MT783) was purchased from Moravek, Brea, Calif.

Cell Lines

Wild type Chinese Hamster Ovary (CHO-WT) cells, CHO cells transfected with FR-β (CHO-FR-β) and human nasopharyngeal epidermoid KB cells, expressing FR-α (American Type Culture Collection, Manassas, Va.) were grown in folic-acid-free RPMI 1640 medium (Gibco, Grand Island, N.Y.), supplemented with 10% foetal calf serum, 2 mM L-glutamine, 0.15 mg/ml proline and 100 units/ml penicillin and streptomycin. [$^3$H]folic acid binding capacities of CHO-FR-β and KB cells were 0.5-1 μmol/$10^6$ cells and 20-40 μmol/$10^6$ cells, respectively. Human monocytic-macrophage THP1 cells (American Type Culture Collection, Manassas, Va.) were grown in RPMI 1640 medium (Gibco, Grand Island, N.Y.) containing 2.2 μM folic acid, supplemented with 10% foetal calf serum, 2 mM L-glutamine, 0.15 mg/ml proline and 100 units/ml penicillin and streptomycin. All cell lines were kept at 37° C. in a humidified atmosphere containing 5% $CO_2$.

Synovial Tissue Samples

In this study we analysed synovial tissue biopsies derived from the knee joints of 15 RA-patients with active disease before treatment and after 4 months of treatment with MTX (starting dose of MTX: 7.5 mg/week; increasing stepwise to 15 mg/week over 12 weeks). Active disease was defined as ≧6 swollen or tender joints and levels of moderate or worse on the physician's and patient's assessments of disease activity (Disease Activity Score-28; DAS-28). All patients had at least 1 clinically involved knee joint. Low dose prednisone (<10 mg/day) and concomitant stable doses of nonsteroidal anti-inflammatory drug (NSAID) treatment were allowed. None of the patients ever used MTX before enrolling the study. In patients taking other DMARDs, the treatment was terminated following a washout phase of 28 days. The arthroscopy procedure was performed as described previously as part of a joint study approved by the Medical Ethics committees of Leiden University Medical Center (Netherlands) and Leeds University Medical Centre (UK). See *Arthritis Rheum.* 2002; 46(8):2034-2038 and 2000; 43(8): 1820-1830 (both Kraan et al.).

As non-inflammatory control synovial tissue we included 7 samples from patients with mechanical joint injury, provided by Dr. B. J. van Royen, department of Orthopedic Surgery, VU University Medical Center, Amsterdam, Netherlands. For peripheral blood sample collection, all patients signed an informed consent form and the study on 'DMARD resistance' was approved by the Medical Ethics committee of the VU University Medical Center, Amsterdam, Netherlands.

FR-β Immunohistochemistry

Immunohistochemical staining of cryostat sections (4 μm) of synovial tissue biopsies from RA patients and controls was performed using a 3-step immunoperoxidase method as described previously. See *Cancer Res.* 2001; 61(8):3458-3464 (Maliepaard et al.) and 2000; 60(18): 5269-5277 (Scheffer et al.). Sections were stained with a specific antibody for FR-β (dilution 1:3000, isotype control: normal rabbit-serum). Macrophages and T-cells were stained with 3A5 (dilution 1:100) and anti-CD3-PE (dilution 1:25; Dako, Glostrup, Denmark) monoclonal antibodies (iso-type control: mouse immunoglobulin), respectively. Biotinylated swine anti-rabbit IgG (Dako; dilution 1:200) and rabbit anti-mouse IgG (Dako; dilution 1:300) were used as secondary antibodies. Colour development was performed using 0.4 mg/ml AEC (aminoethyl carbazole). After counterstaining with haematoxylin, slides were mounted. Stained sections were analysed for FR-β, 3A5 and CD3 expression by digital image analysis, as described previously. See *Arthritis Res. Ther.* 2005; 7(4): R862-R867 (Haringman et al.). In short, for each marker representative regions were used for image acquisition, using 400× magnification. These regions were divided into 6 high-power fields (hpfs) with a 3-pixel overlap. Positive cells were evaluated by analysing 18 consecutive hpfs, scoring numbers of positive cells in the intimal lining layer and the synovial sublining per $mm^2$.

Double-Labelling Immunofluorescence

FR-β was detected by swine-anti-rabbit HRP-labelled antibodies (dilution 1:200; Dako, Glostrup, Denmark) and development was with rhodamine/thyramine (red fluorescence) according to the instructions of the manufacturer (dilution 1:1000). CD68 was detected by goat-anti-mouse biotinylated antibodies (dilution 1:100; Dako, Glostrup, Denmark) utilizing streptavidin Alexa-488 as a substrate (dilution 1:750; green fluorescence; Molecular Probes, Eugene, Oreg.). Slides were mounted with Vectashield, containing 1 μg/ml DAPI (for staining of nuclei) (Vector Laboratories Inc., Burlingame, Calif.). Cells were examined using a fluorescence microscope (Leica DMRB, Rijswijk, Netherlands).

Isolation of Peripheral Blood Cells of RA-Patients and Culture Conditions

Peripheral blood mononuclear cells were isolated from freshly obtained blood samples by gradient centrifugation (35 minutes at 400×g) on Ficoll-Paque Plus (Amersham Pharmacia Biotechnologies, UK). After centrifugation the interphase was carefully collected and washed 3 times using Phosphate Buffered Salt solution (PBS) supplemented with 1% BSA. The lymphocyte fraction was counted and resuspended in IN/IDM culture medium (Invitrogen, Breda, Netherlands) which contained 10% FCS, 2 mM L-glutamine and 100 μg/ml penicillin and streptomycin. Monocytes were isolated by adherence after 2 hours incubation at 37° C. in culture flasks followed by RNA extraction or macrophage differentiation by culturing the monocytes for 7 days in the presence of 10 ng/ml Macrophage Colony Stimulating Factor (M-CSF) (Strathmann Biotech, Hamburg, Germany).

Peripheral blood lymphocytes (PBLs) remaining in suspension after monocyte adherence were collected for RNA isolation or used for T-cell activation by incubating them at a density of 1×$10^6$ cells/ml with monoclonal anti-CD28 (5 μg/ml, CLB-CD28/1, Sanquin, Amsterdam, Netherlands) and anti-CD3 (1 μg/ml, CLB-T3/4.E, Sanquin, Netherlands) in goat anti-mouse (Dako, Glostrup, Denmark) coated 24 well plates. After 48 hours stimulation, activated T-cells were harvested for RNA isolation and the activation status was determined by measuring CD25 expression using flow-cytometry (FACScalibur, Becton & Dickinson).

FR-β mRNA Expression in Synovial Tissue and Peripheral Blood Cells of RA-Patients RNA from synovial tissue (n=7), PBLs (n=9), monocytes (n=9), macrophages (n=25), and activated T-cells (n=22) from RA patients was isolated using the Qiagen RNeasy Plus isolation kit (Qiagen, Venlo, Netherlands) following the instructions provided by the manufacturer. Prior to RNA isolation, the frozen synovial tissue samples were powdered by grinding them in a liquid nitrogen prechilled mortar where after RPE buffer was added. Total RNA concentrations were determined using a Nanodrop ND-1000 spectrophotometer (Nanodrop Technologies, Wilmington, USA). Real-time reverse transcription-PCR (RT-PCR) methodology described previously by was used to measure simultaneously mRNA levels for FR-β and glyceraldehyde-3-phosphate (reference gene). See *Cancer Res.* 2006; 66(11): 5875-5882 (Qi et al.).

The reverse transcription step was carried out using Taqman Reverse Transcript Reagents from Applied Biosystems (Foster City, Calif.), following the protocol of the manufacturer. Briefly, 400 ng of total RNA was mixed with random hexamer primers (50 μmol/L), RNase inhibitor (1 unit/μL), MultiScribe reverse transcriptase (5 units/μL), and deoxynucleoside triphosphates mix (2.5 mmol/L each) in reverse transcriptase buffer. The 10-μL reaction mixture was first incubated at 25° C. for 10 minutes, then at 48° C. for 30 minutes and finally at 95° C. for 5 minutes.

The subsequent real-time PCR step for FR-β was carried out in the presence of 12.5 μL of PCR Mastermix (Applied Biosystems), 0.5 μL, each of forward and reverse primer (CTGGCTCCTTGGCTG-AGTTC, GCCCAGCCTGGT-TATCCA), and 0.5 μl, of Taqman probe (6FAM-TCCTC-CCAGACTACCTGCCCTCAGC-TAMERA). The primers and the Taqman probe for control GAPDH gene were purchased from Applied Biosystems. The PCR conditions were 2 minutes at 50° C., then 10 minutes at 95° C., followed by 40 cycles of 15 seconds each at 95° C., and finally 1 minute at 60° C. Fluorescence data generated were monitored and recorded by the Gene Amp 5700 sequence detection system (Applied Biosystems). All samples were set up in triplicate and normalized to GAPDH values.

Analysis of FR-β/FR-α and RFC Binding Affinity for Novel Generation Folate Antagonists An intact cell binding assay for competitive binding of [$^3$H]-folic acid and novel anti-folate drugs to FR-β and FR-α was performed essentially as described previously. See *Mol. Pharmacol.* 1995; 48: 459-47 and *Cancer Res.* 1995; 55(17): 3795-3802 (both Westerhof et al.). Briefly, CHO-β cells (FR-β transfected Chinese Hamster Ovary cells) and KB cells (FR-α expressing cells) were detached by incubation in PBS+1 mM EDTA. Detached cells were suspended in ice-cold HEPES-buffered saline (140 mM NaCl, 20 mM HEPES, 6 mM KCl, 2 mM $MgCl_2$, 6 mM D-glucose, pH 7.4 with NaOH) to a cell concentration of $3\times10^6$ and $1\times10^6$ cells/ml, respectively. One ml of cell suspension was added to a series of Eppendorf tubes containing 100 μmol [$^3$H]-folic acid (specific radioactivity: 2,000 dpm/μmol) in the absence or presence of increasing concentrations of natural folate or folate antagonists. Following 10 minutes at 4° C., cells were centrifuged in an Eppendorf centrifuge (30 s, 10,000 rpm), the supernatant was aspirated and cell pellets were resuspended in 200 μl water and analysed for radioactivity (Optima Gold scintillation fluid, United Technologies, Packard, Brussels, Belgium). Non-specific binding of [$^3$H] (usually <2% of specific binding) was determined by measuring cell-associated radioactivity in the presence of a 1000-fold molar excess of unlabeled folic acid. Concentrations of natural folates and selected folate antagonists required to displace 50% of [$^3$H] folic acid from FR-β or FR-α were determined and presented as binding affinities relative to folic acid. For comparison, data for affinities of the RFC for natural folates and folate antagonists were presented from previous studies. See Mol Pharmacol 1995; 48: 459-471 Westerhof et al.) and *Cancer Res.* 2005; 65(24): 11721-11728 (Gibbs et al.).

Cell proliferation inhibition assay CHO-WT and CHO-FRβ cells were seeded in individual wells of a 24-well tissue culture plate at a density of $1\times10^4/cm^2$. After 24 hours, 8 concentrations (with 2.5-fold increments) of folate antagonist drugs were added in the absence or presence (to block FR) of 1 μM folic acid. After 72 hours incubation, cells were harvested by trypsinization and counted for cell viability as described before. See *Mol. Pharmacol.* 1999; 55(4): 761-769 (Jansen et al.).

In other experiments human monocytic-macrophage THP1 cells were tested for antiproliferative effects of folate antagonists. To this end, 1 ml of cell suspension containing $1.25\times10^5$ cells were plated in individual wells of a 24-well tissue culture plate and incubated with 8 concentrations (with 2.5-fold increments) of folate antagonist drugs. After 72 hours drug exposure cell counts were performed with a haemocytometer and viability was checked by trypan blue exclusion.

Results

FR-β Synovial Tissue Immunohistochemistry

Immunohistochemical staining of all RA synovial tissue showed high expression of FR-β in the intimal lining layer as well as in the synovial sublining. The staining pattern for FR-β was consistent with 3A5 (macrophage) staining, whereas T-cell areas showed no staining (FIG. 1A-C). In fact, more detailed fluorescence microscopic analysis demonstrated co-localization of FR-β and CD68 (macrophage marker) on the cellular membranes of synovial tissue infiltrating macrophages and intimal macrophages (FIG. 1D-F). In non-inflammatory synovial tissue of orthopaedic controls, no staining for FR-β was observed, consistent with low numbers of macrophages (not shown).

Figure 2:
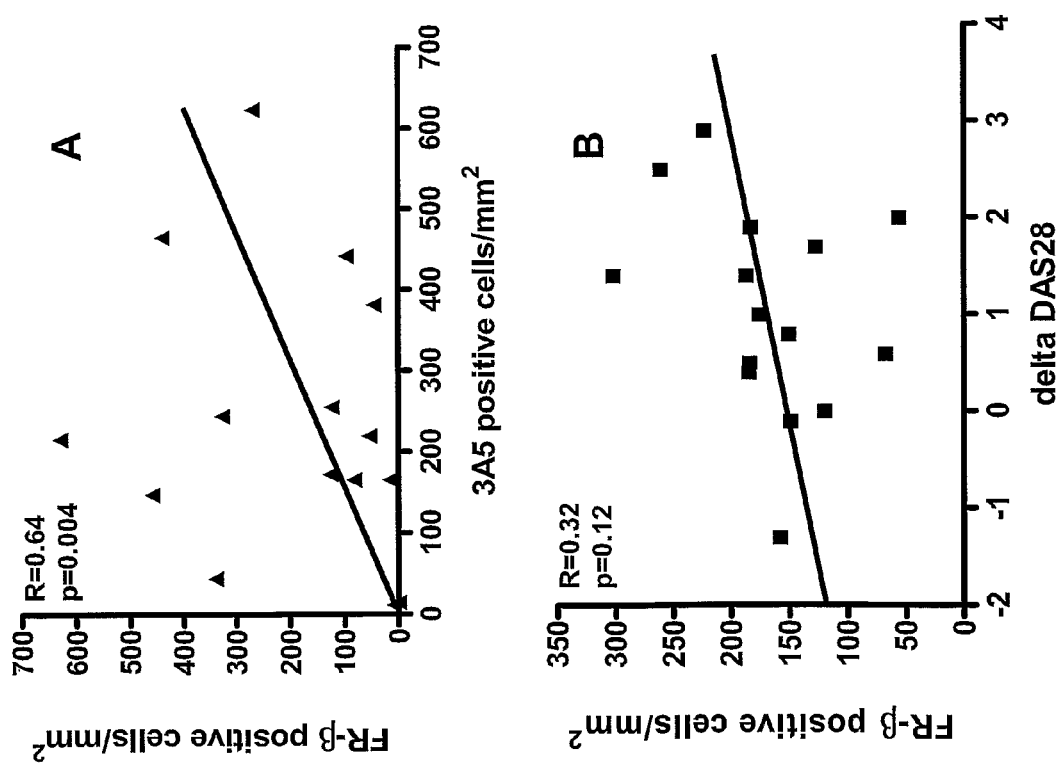
FIG. 2: (A) Correlation between 3A5 (macrophages) and FR-β positive cells/mm$^2$ in synovial tissue of RA patients (n=15) before MTX treatment. Median positive cell counts in the synovial subliming layer/mm$^2$ were 126 (range: 9-630) for FR-β and 219 (range: 11-622) for 3A5. Linear regression: R=0.64; p=0.04. (B) Correlation between DAS28 improvement (ΔDAS28) and FR-β expression on macrophages (positive cells/mm$^2$) after 4 months treatment with MTX (R=0.31; p=0.11).

Staining results were analysed by computer-assisted digital image analysis. A significant correlation was found between 3A5 and FR-β expression in the synovial sublining layer (cell counts/$mm^2$) (p=0.04) (FIG. 2A). Median positive cell counts in the synovial sublining layer/$mm^2$ were 126 (range 9-630) for FR-β and 219 (range 11-622) for 3A5. Median numbers of macrophages decreased upon 4 months of treatment with MTX (from 219 to 119 positive cell counts in the synovial sublining layer/$mm^2$, p=0.14). FR-β expression after 4 months of treatment with MTX was positively correlated (r=0.31) with DAS28 improvement (ΔDAS28), but did not reach statistical significance (p=0.11) (FIG. 2B).

Figure 3:
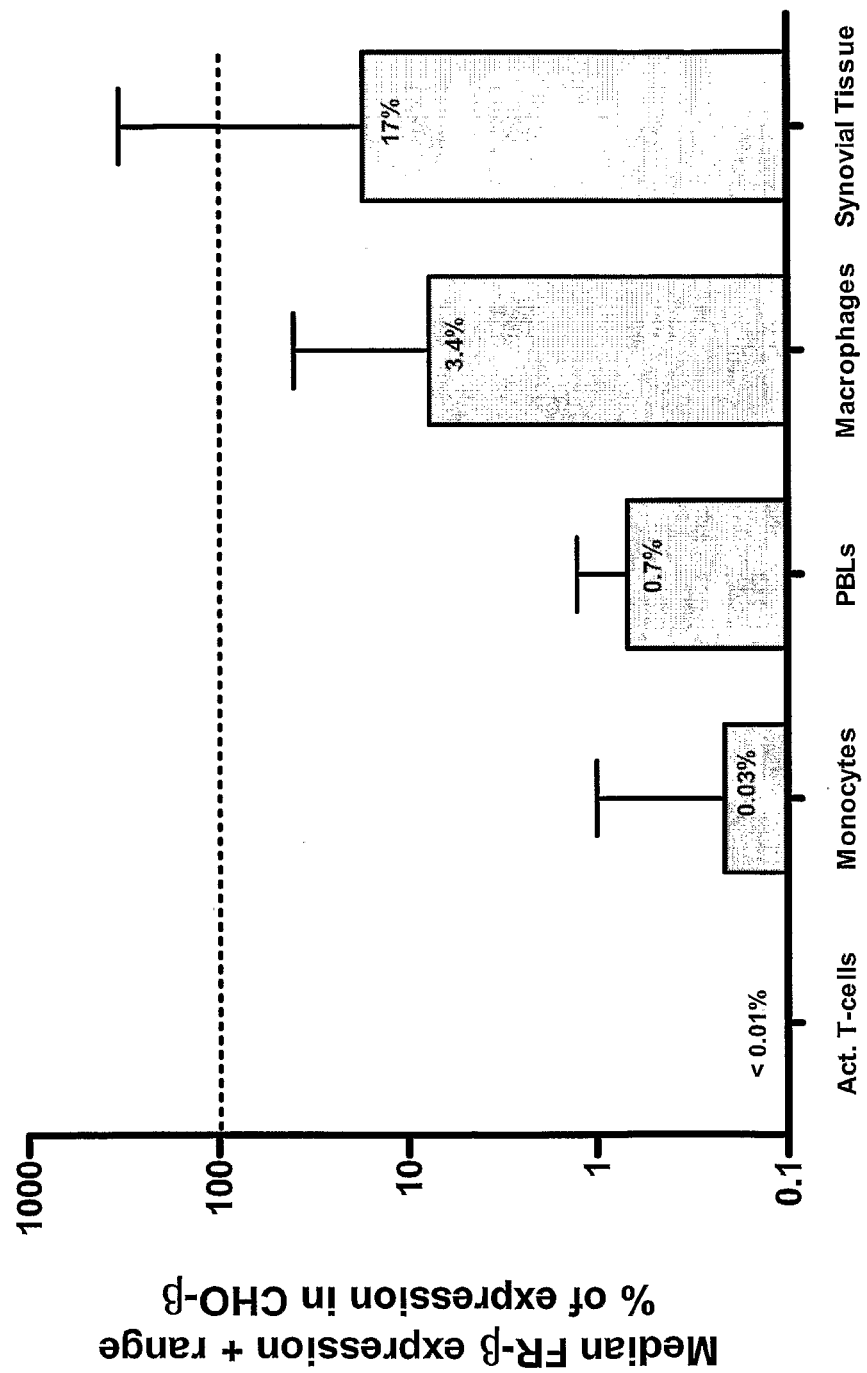
FIG. 3: FR-β mRNA expression in synovial tissue and ex vivo cultured RA Peripheral Blood Lymphocytes (PBLs). Median FR-β mRNA expression was determined in peripheral blood lymphocytes (PBLs; n=9), monocytes (n=9), ex vivo cultured macrophages (n=25), ex vivo activated T-cells (n=22) and synovial tissue of RA patients (n=7). FR-β expression in these samples is shown as a percentage of the expression in CHO-β cells (Chinese Hamster Ovarian cells transfected with FR-β; expression in these cells was set to 1.00).

FR-βmRNA Expression in RA-Synovial Tissue and Peripheral Blood Cells of RA Patients To further confirm the differential expression of FR-β in synovial tissue, FR-β mRNA levels were determined by PCR analysis in synovial tissue biopsies as compared to those in peripheral blood cells of RA-patients, including lymphocytes, ex vivo activated T-cells, and peripheral blood monocytes and ex vivo monocyte-derived macrophages. FR-β mRNA levels were presented relative to CHO-FR-β cells (set at 100%). Ranking of FR-β mRNA expression was highest for RA-synovial tissue (median 17% compared to CHO-β cells)>ex vivo monocyte-derived macrophages (3% compared to CHO-β cells)>peripheral blood lymphocytes (PBLs) (0.7%)>>monocytes (0.02%) and ex vivo activated T-cells (<0.001%) (FIG. 3).

Binding Affinities of FR-β Vs. FR-α for Folate Antagonists

Binding affinities of FRα for selected folate antagonists were previously reported by Westerhof et al. but to what extent they overlap or differ for the FR-β isoform has not been established. To this end, binding affinities by FR-β versus FRα for a series of folate-based inhibitors of DHFR, TS and GARTFase were determined and shown in FIG. 4. With respect to folic acid, both FR-β and FRα displayed a rather low affinity for the group of folate antagonist inhibitors of DHFR. Binding affinity of FR-β for MTX is approximately 50-fold lower than for folic acid. The binding affinity for PT523 is markedly lower than for MTX (0.3% of folic acid)

while PT644, the 5-methyl analogue of PT523, showed an affinity comparable to MTX. Of note, FR-α exhibits a good binding affinity for all tested folate-based TS inhibitors, but binding affinities of FR-β for pemetrexed, raltitrexed and BGC 9331 were markedly lower (16-30 fold) than for FRα. Retention of a high binding affinity of FR-β was observed for the TS inhibitors CB300635 (161% of folic acid) and (6RS)-BGC 945 (89% of folic acid) and (6S)-BGC 945 (46% of folic acid). FR-β also exhibited a proficient binding affinity for the GARTFase inhibitors DDATHF (27% of folic acid) and AG2034 (54% of folic acid) even though FRα binding affinities for these compounds were 2.5-fold higher. Together, these results demonstrate a broad differential in binding affinities of FR-β for folate antagonists, among which several folate antagonists revealed a markedly higher binding affinity than for MTX.

Folate Antagonist Induced Growth Inhibition of FR-β Expressing Cells

Figure 5:
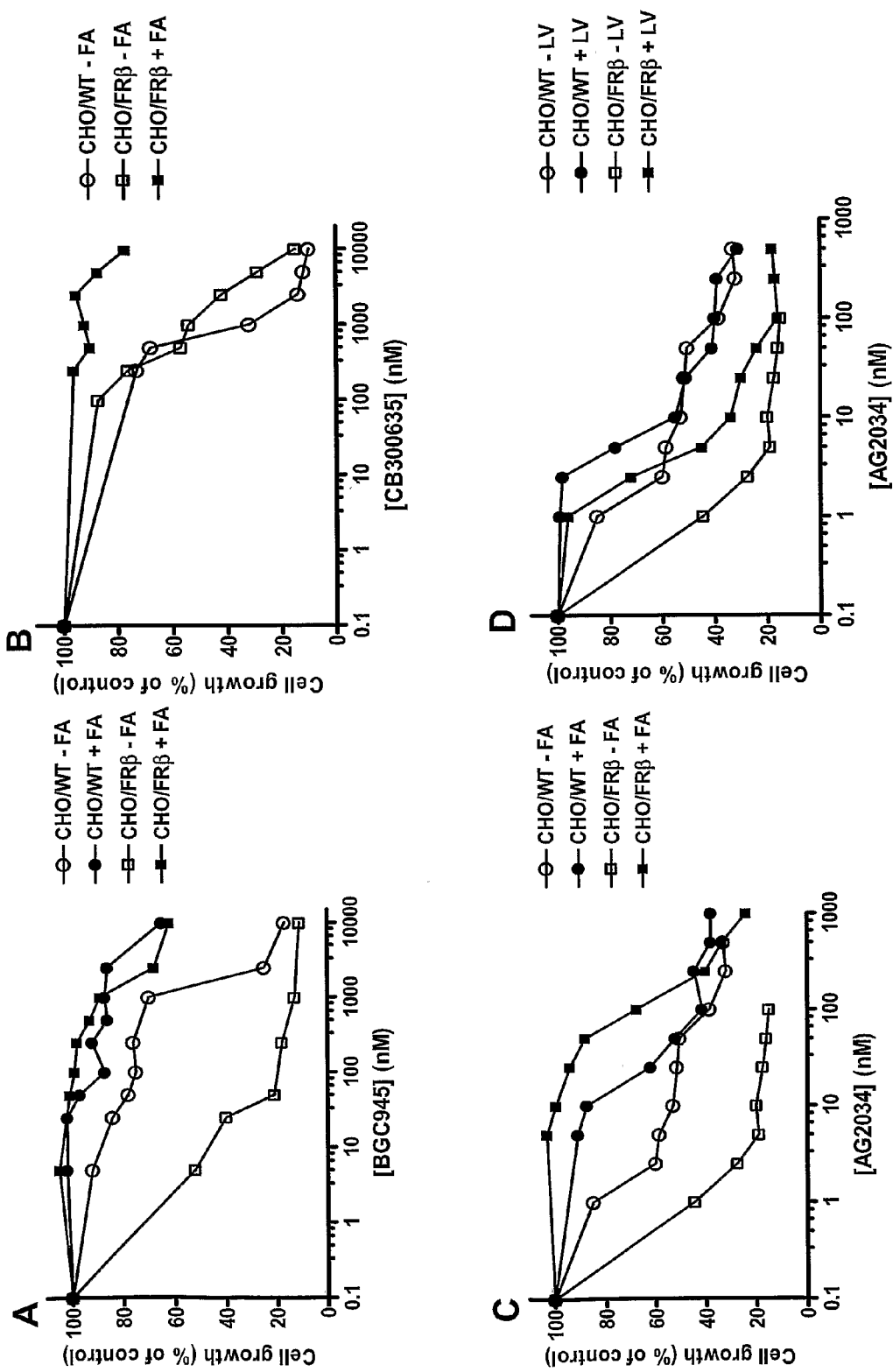
FIG. 5: Growth inhibition of CHO/WT and CHO/FR-β cells by BGC 945 with or without 1 μM folic acid (A), CB300635 (B) and AG2034 (C/D) with or without supplementation of folic acid (1 μM) or leucovorin (20 nM). Results are the mean of 3 experiments (SD<20%).

To investigate whether the folate antagonists used in the current study would all convey a potential growth inhibitory effects against macrophage-like type of cells, this parameter was investigated for human monocytic-macrophage THP1 cells (Table 1). Consistent with RFC as the dominant transport route in THP1 cells, potent growth inhibitory effects were observed for all folate antagonists, except CB300635 and BGC 945, two compounds that have a poor affinity for RFC. Since THP1 cell line model is FR-negative (in contrast to activated synovial macrophage), three folate antagonists for which FR-β displayed the highest binding affinity (CB300635, AG2034 and BGC 945) were evaluated for their potency to target FR-β by provoking cell growth inhibition of CHO-FR-β cells. Against CHO/WT cells, BGC 945 only induced growth inhibition at extracellular concentrations>1000 nM (FIG. 5A). Remarkably, growth inhibition of CHO/FR-β cells was induced at markedly lower concentrations (10-50 nM) of BGC 945. The addition of folic acid to these cell cultures completely abrogated the activity of BGC 945, consistent with a blockade of FR. Despite displaying the highest binding affinity for FR-β, CB300635 was not markedly potent in inducing growth inhibition in CHO/FR-β cells (FIG. 5B). The notion that co-administration of folic acid abrogated activity of CB300635 suggest that FR-β is involved in the cellular uptake of this compound. Finally, AG2034 may utilize both the constitutively expressed RFC and FR as route for cell entry (FIG. 5). As such, AG2034 displayed a growth inhibitory potential against CHO/WT cells and to a greater extent to CHO/FR-β cells (FIG. 5C/D). Consistently, abrogation of AG2034 growth inhibitory effects by FR-β blocking (with folic acid) and RFC blocking (with LV) are only partial (FIG. 5C/D).

Discussion

Since MTX is the anchor-drug in many therapeutic regimens for RA treatment, delineation of genetic, biochemical and metabolic parameters that could assist in predicting and/or improving the therapeutic response to MTX have received considerable recent interest. This study focused specifically on the role of cell membrane transport of MTX, which, in activated synovial macrophages, is mediated predominantly by the folate receptor β isoform. Given the notion that the molecular and functional properties of FRs and the constitutively expressed RFC differ considerably, a better understanding of the properties of FR-β may facilitate a better therapeutic window by selective targeting of FR-β over RFC.

Here we showed that FR-β expression primarily co-localized with macrophages in the intimal lining layer and the synovial sublining of RA patients and may therefore be an attractive target for folate antagonists. Screening for binding affinities of a series of second generation folate antagonists, some of which with proven anticancer activity, revealed that the group of DHFR inhibitors all had a rather low FR-β affinity. This is consistent with previously reported structure activity relationships demonstrating that the α isoform of FR had low affinities for folate antagonists with a 2,4-$NH_2$-based structure (see Table 2). Interestingly, while FRα demonstrated a relatively high binding affinity for all tested folate-based inhibitors of thymidylate synthase, for FR-β this was only retained for 3 compounds (CB300635, GW1843 and BGC 945) that share a common chemical property of 3-ring structures and/or glutamate side chain modifications (see Tables 2 and 3). The latter modification also markedly suppresses its ability to be transported via the RFC and thus contributes to a greater FR-selectivity. In fact, selective targeting by BGC 945 for FR-α and not RFC was demonstrated in FRα over expressing cell lines. In addition to folate-based TS inhibitors, FR-β also exhibited moderate to high binding affinities for folate-based GARTFase inhibitors (AG2034 and DDATHF) which classifies them as folate antagonist drugs that can be transported both via RFC and FR.

Figure 4:
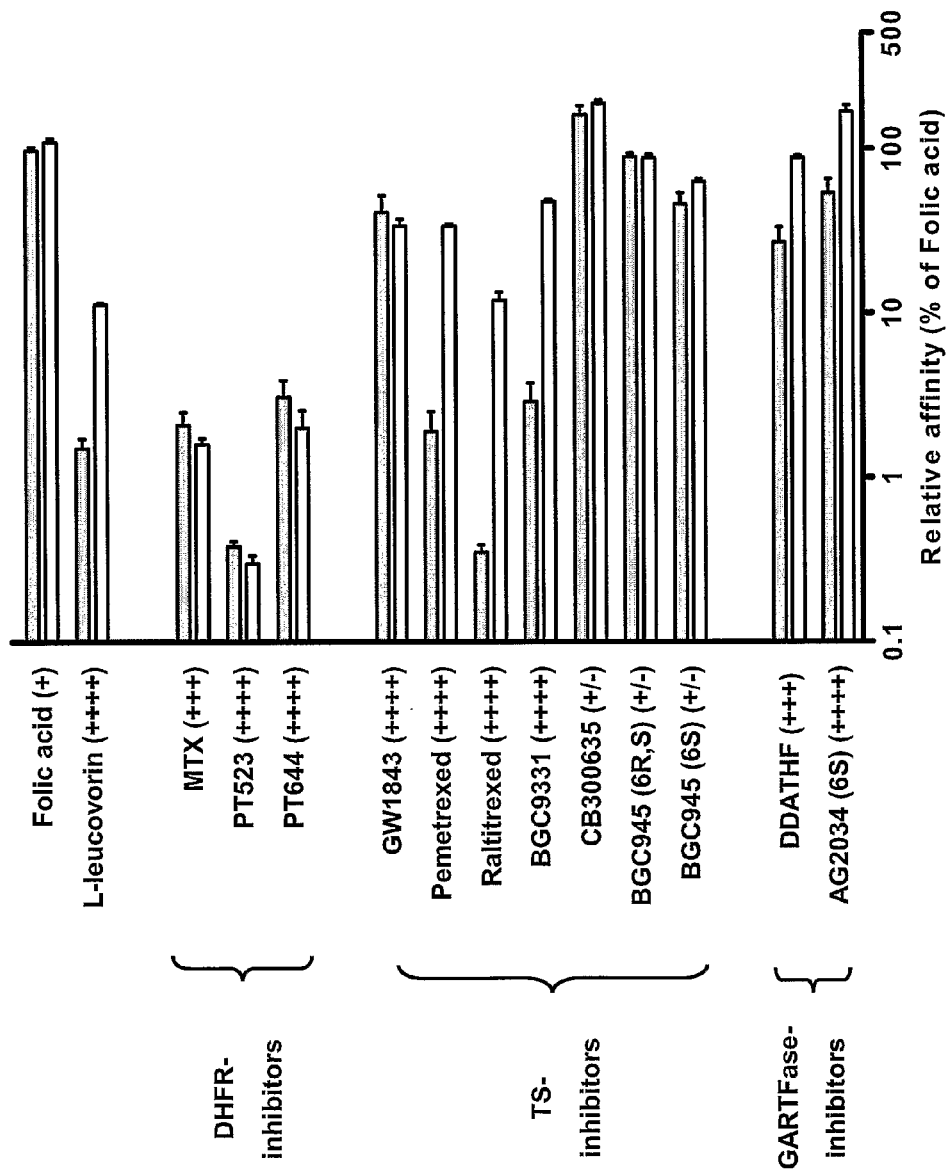
FIG. 4: Relative binding affinities of FR-α (white bars) and FR-β (grey bars) for novel generation folate antagonists. FR-α and FR-β binding affinities of the drugs were determined by [$^3$H]-folic acid displacement of FRα expressing KB-cells and FRβ transfected CHO-β cells as described in the Materials and Methods section. Binding affinities are presented as percentage relative of folic acid binding affinity. Results are the mean±SD of 3-5 separate experiments (SD<30%). For comparison, affinities of RFC for folate antagonists are presented as: ++++(high affinity), +++(moderate affinity), ++(low affinity), +(poor affinity), +/− (very poor affinity) based on previously published data.

FR-β-transfected CHO cells were used as a model system to evaluate the efficiency of FR-β-mediated cellular uptake of folate antagonists by conveying anti-proliferative effects. This cell line model may be clinically representative, based on [$^3$H]-folic acid binding levels and FR-β mRNA levels that are compatible with FR-β mRNA levels in synovial tissue of RA patients (FIG. 4). The largest differential in activity between control (RFC-expressing) CHO cells and FR-β transfected cells was observed for BGC 945, consistent with a poor affinity for transport via RFC and a high FR-β binding affinity. FR-β mediated uptake of BGC 945 could be inhibited by blocking of the receptor with excess folic acid, implying that circulating natural folates in synovial tissue/plasma could attenuate the potential activity of BGC 945 in vivo either by receptor occupancy/competition or by receptor down-regulation.

Example 2

Compounds of the Invention

Table 3 shows the structures of the following compounds of the invention:

| | |
|---|---|
| CB300638 (BGC 638) | CB300944 |
| (6S)-CB300638 | CB300945 (BGC 945) |
| CB300935 | (6S)-CB300945 |
| CB300936 | CB300947 |
| CB300940 | CB300951 |

These were prepared according to the methods given in WO 94/11354 A1, WO 03/020300 A1, WO 03/020706 A1, WO 03/020748 A1, *J. Med. Chem.*, 2000, 43, 1910-1926, *Tetrahedron*, 63 (7), 2007, 1537-1543 (Bavetsias et al.) and *Cancer Research* 65, 2005, 11721-11728 (Gibbs et al.).

Example 3

Formulation

The following illustrate representative pharmaceutical dosage forms containing a cyclopenta[g]quinazoline of formula (I), particularly in pharmaceutically acceptable salt form, for therapeutic or prophylactic use in humans:

| (a) Tablet I | mg/tablet |
|---|---|
| Cyclopenta[g]quinazoline salt | 100 |
| Lactose Ph. Eur. | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Cyclopenta[g]quinazoline salt | 50 |
| Lactose Ph. Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Cyclopenta[g]quinazoline salt | 1.0 |
| Lactose Ph. Eur. | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Cyclopenta[g]quinazoline salt | 10.0 |
| Lactose Ph. Eur. | 488.5 |
| Magnesium stearate | 1.5 |

| (e) Injection I | (50 mg/ml) |
|---|---|
| Cyclopenta[g]quinazoline salt | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Cyclopenta[g]quinazoline salt | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Cyclopenta[g]quinazoline salt | 0.1% w/v |
| Sodium phosphate BP | 2.26% w/v |
| Citric acid | 0.38% w/v |
| Polyethylene glycol 400 | 3.5% w/v |
| Water for injection to 100% | |

The above formulations may be prepared by conventional procedures well known in the pharmaceutical art. The tablets (a) to (c) may be enteric coated by conventional means, for example with a coating of cellulose acetate phthalate.

TABLE 1

Growth inhibitory effects of folate antagonists against human monocytic-macrophage THP1 cells[#]

| Folate antagonist | $IC_{50}$(nM) |
|---|---|
| MTX | 7.1 ± 0.5 |
| PT523 | 2.2 ± 0.3 |
| PT644 | 1.0 ± 0.4 |
| Raltitrexed | 2.4 ± 0.5 |
| Pemetrexed | 10.7 ± 2.2 |
| GW1843 | 1.6 ± 0.1 |
| BGC 9331 | 8.7 ± 0.8 |
| CB300635 | 4850 ± 285 |
| BGC 945 | 3630 ± 350 |
| DDATHF | 9.8 ± 0.8 |
| AG2034 | 3.2 ± 0.2 |

[#]THP-1 cells were grown in RPMI-1640 medium containing 2.2 µM folic acid (which would block any FR activity.
Drug exposure time; 72 hours. Results are the mean ± S.D. of 3 separate experiments.

TABLE 2

Structures of comparative compounds

| Designation | Structure |
|---|---|
| Folic acid | 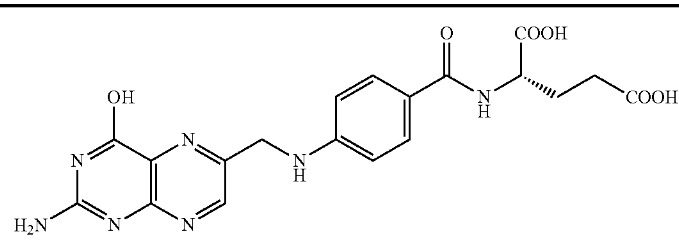 |
| Leucovorin | 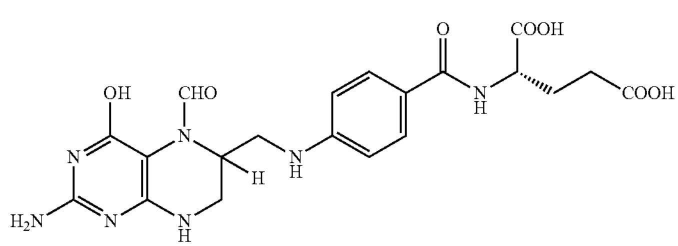 [SMILES: Nc1nc(O)c2c(n1)NCC(CNc1ccc(C(=O)N[C@@H](CCC(=O)O)C(=O)O)cc1)N2C=O] |

TABLE 2-continued
Structures of comparative compounds
| Designation | Structure |
| --- | --- |
| MTX | 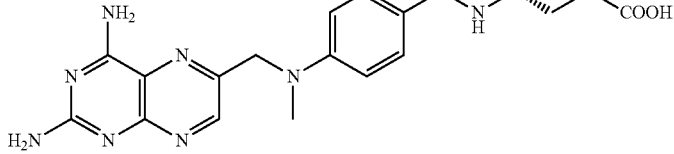 |
| PT523 | 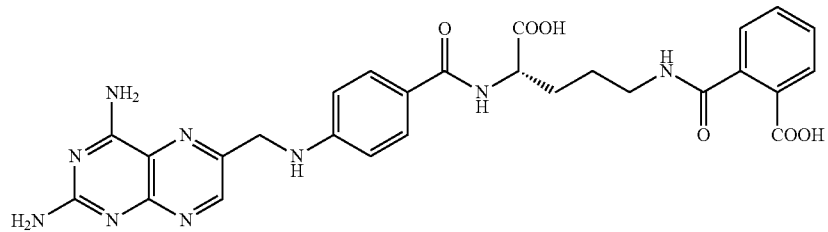 [SMILES: Nc1nc(N)c2nc(CNc3ccc(C(=O)N[C@@H](CCCNC(=O)c4ccccc4C(=O)O)C(=O)O)cc3)cnc2n1] |
| PT644 | 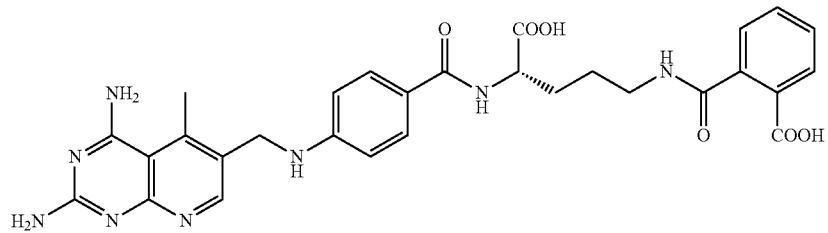 [SMILES: Cc1c(CNc2ccc(C(=O)N[C@@H](CCCNC(=O)c3ccccc3C(=O)O)C(=O)O)cc2)cnc2nc(N)nc(N)c12] |
| GW1843 | 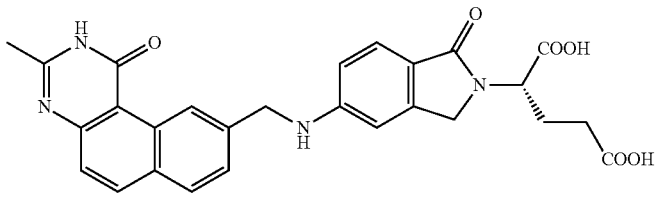 [SMILES: Cc1nc2ccc3ccc(CNc4ccc5c(c4)CN([C@@H](CCC(=O)O)C(=O)O)C5=O)cc3c2c(=O)[nH]1] |
| Pemetrexed | 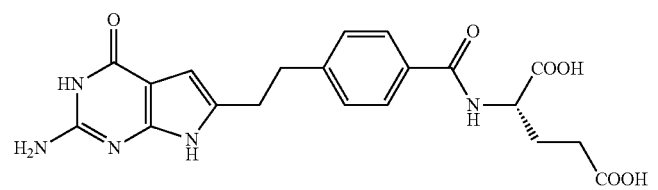 [SMILES: Nc1nc2[nH]c(CCc3ccc(C(=O)N[C@@H](CCC(=O)O)C(=O)O)cc3)cc2c(=O)[nH]1] |
| Raltitrexed | 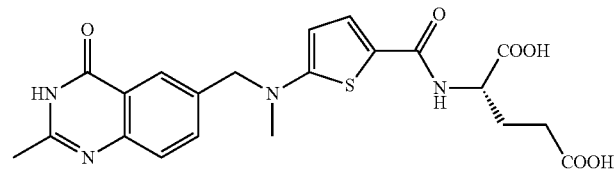 [SMILES: Cc1nc2ccc(CN(C)c3ccc(C(=O)N[C@@H](CCC(=O)O)C(=O)O)s3)cc2c(=O)[nH]1] |
| BGC 9331 | 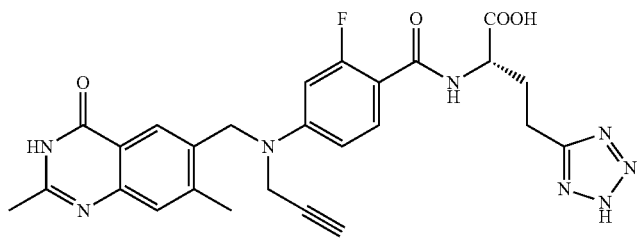 [SMILES: C#CCN(Cc1cc2c(=O)[nH]c(C)nc2cc1C)c1ccc(C(=O)N[C@@H](CCc2nn[nH]n2)C(=O)O)c(F)c1] |

TABLE 2-continued
Structures of comparative compounds
| Designation | Structure |
|---|---|
| CB300635 | 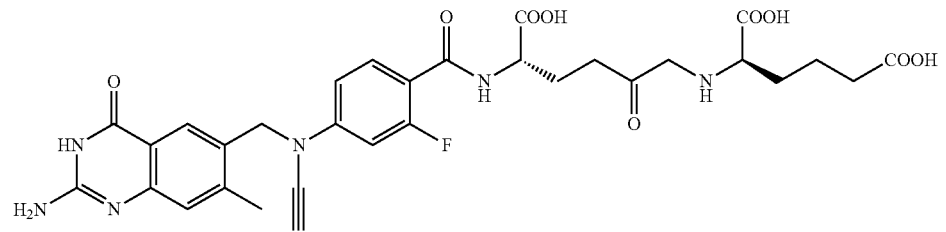 [SMILES: C#CN(Cc1cc2c(=O)[nH]c(N)nc2cc1C)c1ccc(C(=O)N[C@@H](CCC(=O)CN[C@H](CCCC(=O)O)C(=O)O)C(=O)O)c(F)c1] |
| DDATHF | 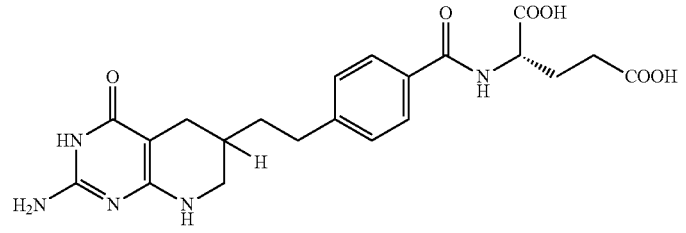 [SMILES: Nc1nc2c(c(=O)[nH]1)CC(CCc1ccc(C(=O)N[C@@H](CCC(=O)O)C(=O)O)cc1)CN2] |
| AG2034 | 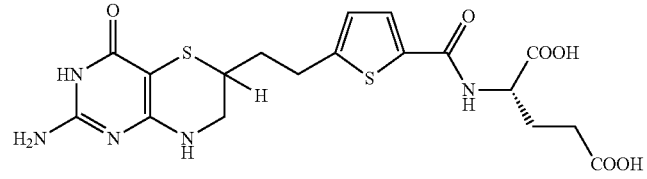 [SMILES: Nc1nc2c(c(=O)[nH]1)SC(CCc1ccc(C(=O)N[C@@H](CCC(=O)O)C(=O)O)s1)CN2] |
TABLE 3
Structures of the compounds of the invention
| CB300638 | 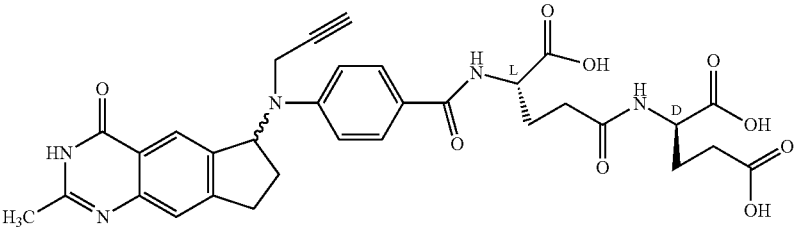 |
|---|---|
| (6S)-CB300638 | 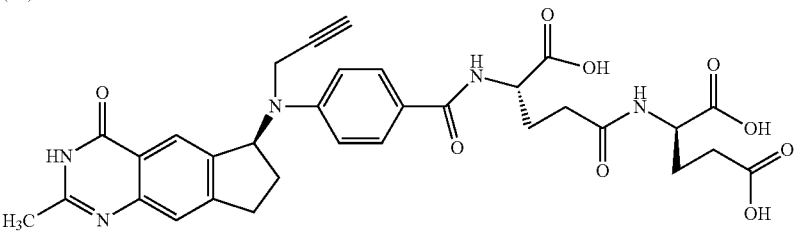 |
| CB300935 | 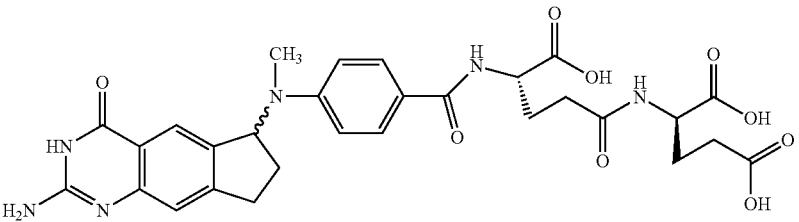 |

TABLE 3-continued
Structures of the compounds of the invention
CB300936
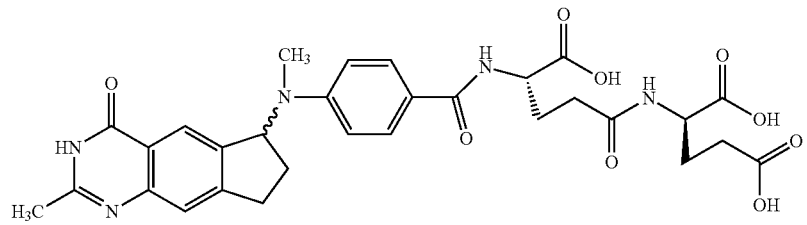 [SMILES: CN(c1ccc(C(=O)N[C@@H](CCC(=O)N[C@H](CCC(=O)O)C(=O)O)C(=O)O)cc1)C1CCc2cc3nc(N)[nH]c(=O)c3cc21]
CB300940
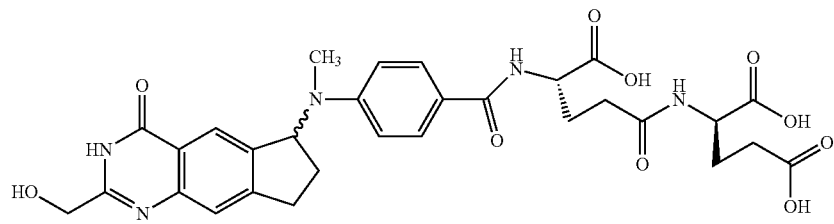 [SMILES: CN(c1ccc(C(=O)N[C@@H](CCC(=O)N[C@H](CCC(=O)O)C(=O)O)C(=O)O)cc1)C1CCc2cc3nc(CO)[nH]c(=O)c3cc21]
CB300944
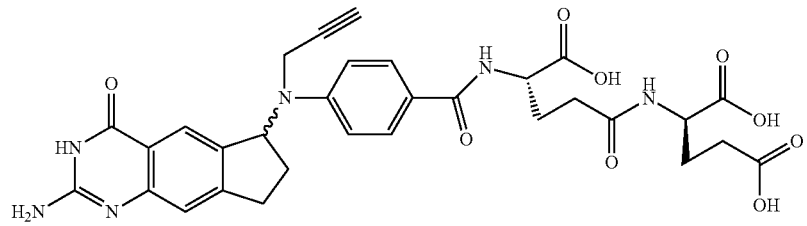 [SMILES: C#CCN(c1ccc(C(=O)N[C@@H](CCC(=O)N[C@H](CCC(=O)O)C(=O)O)C(=O)O)cc1)C1CCc2cc3nc(N)[nH]c(=O)c3cc21]
CB300945 (BGC 945)
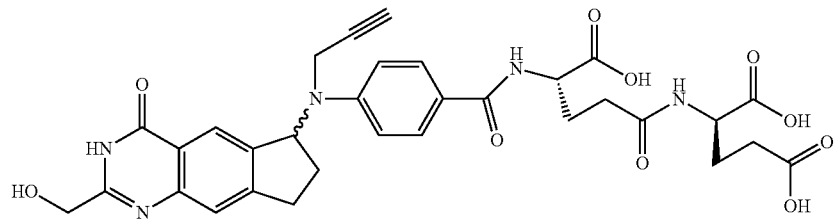 [SMILES: C#CCN(c1ccc(C(=O)N[C@@H](CCC(=O)N[C@H](CCC(=O)O)C(=O)O)C(=O)O)cc1)C1CCc2cc3nc(CO)[nH]c(=O)c3cc21]
(6S)-CB300945
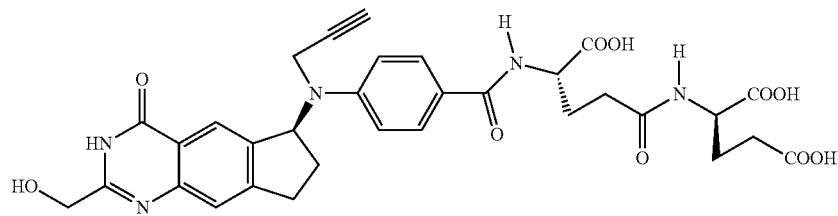 [SMILES: C#CCN(c1ccc(C(=O)N[C@@H](CCC(=O)N[C@H](CCC(=O)O)C(=O)O)C(=O)O)cc1)[C@H]1CCc2cc3nc(CO)[nH]c(=O)c3cc21]
CB300947
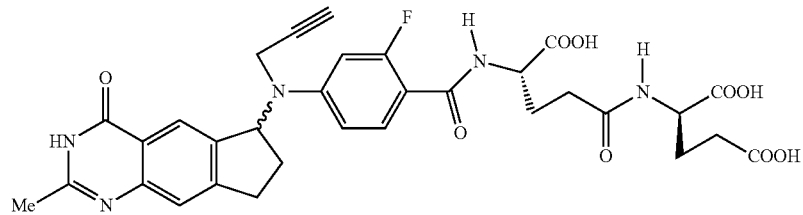 [SMILES: C#CCN(c1ccc(C(=O)N[C@@H](CCC(=O)N[C@H](CCC(=O)O)C(=O)O)C(=O)O)c(F)c1)C1CCc2cc3nc(C)[nH]c(=O)c3cc21]

TABLE 3-continued

Structures of the compounds of the invention

CB300951

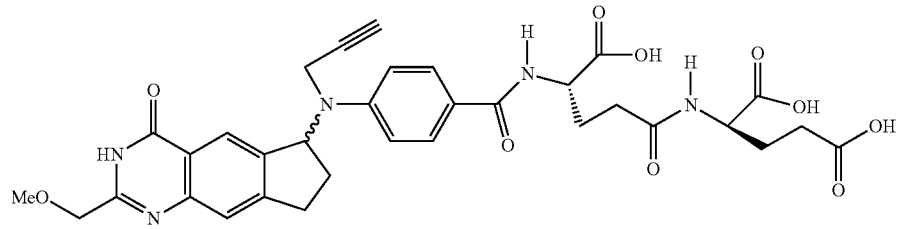 [SMILES: C#CCN(c1ccc(C(=O)N[C@@H](CCC(=O)N[C@H](CCC(=O)O)C(=O)O)C(=O)O)cc1)C1CCc2cc3nc(COC)[nH]c(=O)c3cc21]

The invention claimed is:

1. A method for treating myeloid leukaemia wherein the myeloid leukaemia cells express β-folate receptors in a patient in need of such treatment which comprises administering to said patient an effective amount of a cyclopenta[g]quinazoline derivative, containing an L-Glu-γ-D-Glu dipeptide group, of formula (I):

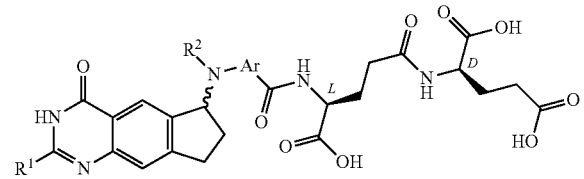

wherein:

$R^1$ is amino, $C_{1-4}$ alkyl, $C_{1-4}$ hydroxyalkyl, $C_{1-4}$ fluoroalkyl or methoxy-$C_{1-4}$-alkyl;

$R^2$ is hydrogren, $C_{1-4}$ alkyl, $C_{3-4}$ alkenyl, $C_{3-4}$ alkynyl, $C_{2-4}$ hydroxyalkyl $C_{2-4}$ halogenoalkyl or $C_{1-4}$ cyanoalkyl; and Ar is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy;

the compound (I) optionally being in the form of a pharmaceutically acceptable salt or ester.

2. A method as claimed in claim 1 wherein $R^1$ is $C_{1-4}$ alkyl or $C_{1-4}$ hydroxyalkyl.

3. A method as claimed in claim 1 wherein $R^1$ is methyl or hydroxymethyl.

4. A method as claimed in claim 1 wherein $R^2$ is methyl, ethyl, propyl, prop-2-enyl, prop-2-ynyl, 2-hydroxyethyl, 2-fluoroethyl, 2-bromoethyl or 2-cyanoethyl.

5. A method as claimed in claim 1, wherein $R^2$ is methyl or prop-2-ynyl.

6. A method as claimed in claim 1 wherein Ar is 1,4-phenylene which may optionally bear one or two substituents selected from the group consisting of chloro and especially fluoro, thiophene-2,5-diyl, thiazole-2,5-diyl or pyridine-2,5-diyl.

7. A method as claimed in claim 1 wherein Ar is 1,4-phenylene, 1,4-phenylene having a 2-fluoro substituent or pyridine 2,5-diyl.

8. A method as claimed in claim 1 wherein Ar is 1,4-phenylene or 2-fluoro-1,4-phenylene.

9. A method as claimed in claim 1 wherein the cyclopenta[g]quinazoline derivative is selected from:

N-{N-{4-[N-(2-methyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid; or N-{N-{4-[N-(2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid;

or a pharmaceutically acceptable salt or ester thereof.

10. A method as claimed in claim 9 wherein the cyclopenta[g]quinazoline derivative is present as its 6S isomer.

11. A method as claimed in claim 1 wherein the cyclopenta[g]quinazoline derivative is administered together with a pharmaceutically acceptable diluent or carrier.

12. A method as claimed in claim 1 wherein the myeloid leukaemia is acute myeloid leukaemia.

13. A method as claimed in claim 1 wherein the myeloid leukaemia is chronic myeloid leukaemia.

* * * * *